United States Patent [19]

Wood

[11] 4,061,664
[45] Dec. 6, 1977

[54] PREPARATION OF PHENOXYBENZYL ESTERS

[75] Inventor: Derek A. Wood, Sittingbourne, England

[73] Assignee: Shell Oil Company, Houston, Tex.

[21] Appl. No.: 737,312

[22] Filed: Nov. 1, 1976

[30] Foreign Application Priority Data

Nov. 12, 1975 United Kingdom ............... 46700/75

[51] Int. Cl.$^2$ ...................... C07C 67/10; C07C 69/74; C07C 69/76; C07C 121/66
[52] U.S. Cl. ................................ 260/465 D; 260/338; 560/124; 560/121; 560/123; 560/55; 560/105
[58] Field of Search .......... 260/468 H, 465 D, 476 R, 260/567.6 M, 473 R

[56] References Cited

U.S. PATENT DOCUMENTS

| 3,666,789 | 5/1972 | Itaya et al. ........................ 260/468 H |
| 3,931,290 | 1/1976 | Bourgau et al. ................. 260/476 R |

FOREIGN PATENT DOCUMENTS 912,104  12/1962  United Kingdom.

OTHER PUBLICATIONS

Hennis et al., I & EC Product Research Development, vol. 7, No. 2, June 1968, pp. 96–101.

Primary Examiner—Dolph H. Torrence

[57] ABSTRACT

Phenoxybenzyl esters are prepared by neutralizing an aqueous solution of a carboxylic acid and contacting the neutralized solution with a solution of phenoxybenzyl halide in a water-immiscible base in the presence of a phase transfer catalyst.

5 Claims, No Drawings

PREPARATION OF PHENOXYBENZYL ESTERS

FIELD OF THE INVENTION

This invention relates to an improved process for preparing phenoxybenzyl esters of cyclopropane carboxylic acids or phenylacetic acids, these compounds being very active as pesticides and forming part of the group of compounds known as "synthetic pyrethroids".

SUMMARY OF THE INVENTION

Accordingly the present invention provides a process for the preparation of a phenoxybenzyl ester of formula (I)

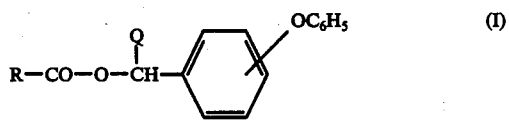

wherein an acid of formula R - COOH in which R represents an optionally substituted cyclopropyl group or an optionally substituted benzyl group is neutralized with a water-soluble base, and then contacted with a solution in a substantially water-immiscible organic solvent of a benzyl halide of formula

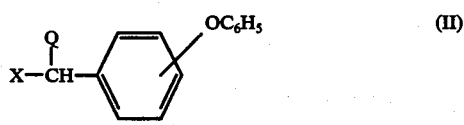

in which X represents a halogen, preferably chlorine or bromine, atom; and Q represents a hydrogen atom or cyano group in the presence of a phase-transfer catalyst.

The neutralisation of the aqueous acid solution can be effected by the use of any water-soluble base, but for reasons of convenience and economics it is usually preferred to use an inorganic base such as potassium carbonate or hydroxide or sodium hydroxide.

Although any substantially water-immiscible organic liquid may theoretically be used as solvent for the benzyl halide, it is generally preferable to use an organic liquid in which the benzyl halide is at least moderately soluble. Futhermore, eventual recovery of the ester product is often simplified if the organic liquid solvent is lighter than water. Suitable solvents include aromatic hydrocarbons such as benzene and toluene or petroleum ether, and it may be convenient to use mixed with hydrocarbons such as xylenes, trimethylbenzene or kerosene as the benzyl halide solvent since the resulting solution of ester can then be employed directly, without isolation of the ester, in the production of a pesticidal emulsifiable concentrate. The reactant solutions are contacted with each other as by agitating, stirring or the like.

The phase-transfer catalyst may be any reagent which will accelerate interphase reactions in aqueous/organic two-phase systems, the most convenient such catalysts including quaternary ammonium and phosphonium salts. Generally economic considerations make it preferable to use quaternary ammonium salts. The quaternary ammonium salts have four hydrocarbyl groups - which optionally may be substituted - attached to the nitrogen atom, for example, aromatic, aliphatic, cycloaliphatic or unsaturated groups or combinations of any of these groups, for example an aromatic-aliphatic group. The cation of the tetrahydrocarbylammonium salt may contain one or more quaternary bound nitrogen atoms. The salt may have any anion; chlorides and bromides are preferred. The total number of carbon atoms in the four hydrocarbyl groups is preferably from 12 to 70. Examples of suitable tetrahydrocarbylammonium salts are tetraalkylammonium halides such as tetra-n-butylammonium chloride, tetra-n-pentylammonium chloride, ethyl-tri-sec-otylammonium chloride, ethyl-tri-n-hexylammonium chloride, n-hexadecyltri-n-hexylammonium chloride, di-n-undecyldiethylammonium chloride and tetra-n-octylammonium chloride, or aryltrialkylammonium halides such as benxyltri-n-butylammonium chloride and the corresponding bromides. The corresponding phosphonium compounds are also useful. Tetra-alkyl ammonium halides are particularly preferred. Alternatively, the macrocyclic polyethers known as "crown ethers" may be utilized as phase transfer catalyst. These compounds, together with their preparation, are described in the literature, for example in Tetrahedron Letters No. 18 (1972) pp. 1793–1796, and are commonly designated by reference to the total number of atoms forming the macrocyclic ring together with the number of oxygen atoms in that ring. Thus the macrocyclic polyether whose formal chemical name is 1,4,7,10,13,16-hexaoxacyclooctadecane is designated as "18-crown-6". Further suitable macrocyclic polyethers are described in U.S. Pat. No. 3,562,295 British Pat. No. 1,108,921 and in co-pending British patent application 10,744/75. Other types of compound which may be used as the phase-transfer catalyst include quaternary ammonium anion exchange resins (suitably in the hydroxyl form) as shown for example in U.S. Pat. No. 3,917,667.

The concentration of catalyst used may widely, but at low concentrations (e.g. 1mole % or less) a higher reaction temperature is required to complete the esterification reaction within an acceptable period of time, whilst the use of higher concentrations (e.g. above 10 mole %) naturally increases the cost of the catalyst required to produce a given quantity of ester. For example, the use of 5 mole % of catalyst at 65°–70° C will lead to a 20–30 fold reaction in reaction time as compared with the same reagent concentrations at room temperature, and reduction of the catalyst concentration to 1 mole % increases the reaction time 2-3 fold. Thus, the choice of reaction temperature and catalyst concentration are mutually interdependent, and in any individual instance will depend on the local economic factors.

In the phenoxybenzyl esters of formula (I), R is preferably i. a cyclopropyl group of formula (III)

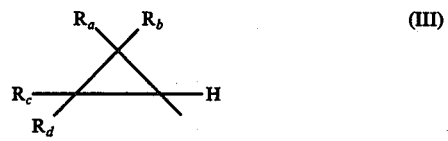

wherein $R_a$ and $R_b$ each represent an alkyl group having from 1 to 6 carbon atoms, especially methyl, or a halogen atom of atomic number 9–35, inclusive, especially a chlorine atom; or $R_a$ and $R_b$ together represent an alkylene group having from 2 to 6, especially 3, carbon atoms; or $R_a$ represents a hydrogen atom and $R_b$ represents an alkenyl group having from 2 to 6 carbon atoms, especially an isobutenyl group, or an haloakenyl group having from 2 to 6 carbon atoms and from 1 to 3 chlorine or bromine atoms, especially a mono- or dichlorovinyl group; $R_c$ and $R_d$ each represent an alkyl group having 1 to 6 carbon atoms, especially methyl, or $R_c$ is hydrogen and $R_d$ is an alkenyl group having from 2 to 6 carbon atoms, especially an isobutenyl group, or an haloalkenyl group having from 2 to 6 carbon atoms and from 1 to 3 chlorine or bromine atoms, especially a mono- or dichlorovinyl group; or $R_c$ and $R_d$ together represent an alkylene group having from 2 to 6, especially 3 carbon atoms; or (ii) a benzyl group of formula (IV)

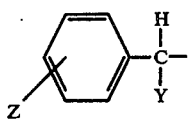

wherein Z represents a halogen atom of atomic number 9-35, inclusive, preferably a chlorine atom, or an alkoxy group of 1 to 4 carbon atoms, e.g. methoxy, and Y represents an alkyl group of 1 to 6 carbon atoms, especially a branched chain group such as in isopropyl group. The phenoxy substituent in the phenoxybenzyl esters of general formula (I) is preferably in the 3-position.

It will be appreciated that as a result of the asymmetric carbon atoms and double bonds which may be present in the phenoxybenzyl esters prepared by the process according to the present invention, the esters can exist in a number of stereoisomeric forms and therefore the present invention also extends to the production of any one or a mixture of such stereoisomers. The required stereoisomer or mixture of stereoisomers may be obtained by using as starting material the appropriate stereoisomeric carboxylic acid and/or the appropriate stereoisomeric phenoxybenzyl halide.

The process of this invention is of particular value in its application to the preparation of alpha-cyano-3-phenoxybenzyl esters of tetramethylcyclopropane carboxylic acid, dimethyl-dichlorovinyl-cyclopropane carboxylic acid, dimethyl-dibromovinyl-cyclopropane carboxylic acid and 2-(4-chlorophenyl)-3-methylbutyric acid, because these esters have interesting pesticidal, especially insecticidal, activity.

In this application the process offers certain advantages over a conventional esterification process using no phase-transfer catalyst. Thus, for example, a conventional process normally produces significant amounts of impurities (such as the olefin formed by hydrogen halide elimination between 2 molecules of benzyl halide) whose removal requires an expensive crystallisation procedure. Use of the phase-transfer catalyst according to the present invention yields a product less contaminated with these impurities. Furthermore, use of the phase-transfer catalyst also facilitates operation of the process at higher reactant concentrations and because the organic solvent used for the benzyl halide can be the same as that required in a pesticidal emulsifiable concentrate, it is possible, using the process of this invention, to produce the final ester as an organic solution which can be transformed directly (i.e. without any further work-up) into a pesticidal emulsifiable concentrate by the addition of appropriate surfactants.

The invention is illustrated in the following Examples.

EXAMPLE 1

A solution of 2,2,3,3-tetramethylcyclopropane carboxylic acid (470g; 3.3M) in water (1200 ml) and potassium carbonate (228g; 1.65M) was treated with a solution of alpha-cyano-3-phenoxybenzyl bromide (864g; 3.0M) in toluene (1500 ml) and the phase-transfer catalyst, tetrabutylammonium bromide, (48g; 5 mole %). The mixture was vigorously stirred and heated to 30° C. The rate of reaction and the completion was determined by thin layer chromatography using Merck pre-coated plates (silica-gel 60F-254), developed in the following solvent mixture: - ethyl acetate 1 vol, chloroform 2 vols. and hexane 7 vols. The reaction was continued until no benzyl bromide could be detected by U.V. light.

When the reaction was complete (after about 24 hours), the aqueous phase was separated and the toluene solution washed with 5% aqueous potassium carbonate solution (2 × 1 liter portions), water (2 × 1 liter portions), and then filtered through a pad of silica-gel (100g). The solution was evaporated under reduced pressure and degassed under high vacuum (0.1mm Hg at 50° C) to give the crude product (1070g, purity 92%). The crude product was up-graded by dissolving in methanol (2 liters) and crystallised with stirring and cooling. A filter-stick was then inserted and the mother-liquors (1230 ml) removed by suction. The residual solid in the reactor was melted, evaporated, and finally degassed under high vacuum to give alpha-cyano-3-phenoxybenzyl 2,2,3,3-tetramethylcyclopropane carboxylate (953g, purity = 95%).

Yield purified product was 86.4% based on starting benzyl bromide.

EXAMPLE 2

A mixture of 2,2,3,3-tetramethylcyclopropane carboxylic acid (7.8g, 0.055M), potassium carbonate (3.8g, 0.0275M) water (40 mls), tetrabutylammonium bromide (1.5g, 10 mole %), alpha-cyano-3-phenoxybenzyl bromide (14.4g, 0.05 mole) and toluene (50 ml) was stirred at 25° C for 5 hours. The aqueous phase was separated and the toluene layer washed twice with 5% potassium carbonate solution and twice with water. The solution was filtered through a pad of silica-gel (3g) and evaporated to leave a pale-yellow oil (17.4g; purity = 92%). Recrystallisation of this material from hexane gave pure alpha-cyano-3-phenoxybenzyl 2,2,3,3-tetramethylcyclopropane carboxylate, melting point 50°-51° C.

Similar experiments carried out at different temperatures and using different concentrations of phase-transfer catalyst showed that complete reaction required 1 hour at 65° C for a 5 mole % catalyst or 3 hours at 70° C for 1 mole % catalyst.

EXAMPLE 3

A mixture of 2-(4-chlorophenyl)-3-methylbutyric acid (703g, 3.3M), water (1500 ml), potassium carbonate (228g, 1.65M) and tetrabutylammonium bromide (48g, 5 mole %) was treated with a solution of alpha-cyano-3-phenoxybenzyl bromide (864g, 3.0M) in toluene (1500 ml). The mixture was vigorously stirred and heated to 35° C. The rate of reaction was followed and completion determined by thin layer chromatography using Merck pre-coated plates (silica-gel 60 F-254), developed in a solvent mixture of ethyl acetate 1 vol., chloroform 2 vols., hexane 7 vols. The reaction was continued until no bromonitrile could be detected by U.V. light.

When the reaction was complete (about 60 hours), the aqueous phase was separated and the toluene layer washed with 5% aqueous potassium carbonate (2 × 1 liter portions), water (2 × 1 liter portions) and then filtered through a pad of silica-gel (100g).

The resulting solution was evaporated under reduced pressure and finally degassed under high vacuum (0.1 mm Hg at 50° C) to give alpha-cyano-3-phenoxybenzyl-2-(4-chlorophenyl)-3-methyl butyrate (1258g; purity = 98%).

Yield based on benzyl bromide was 98%.

EXAMPLE 4

A mixture of 2-(4-chlorophenyl)-3-methylbutyric acid (11.68g, 0.055M), potassium carbonate (3.79g, 0.0275M), water (50 ml), alpha-cyano-3-phenoxybenzyl bromide (14.4g, 0.05M), toluene (50 ml), and tetrabutylammonium bromide (1.5g, 10 mole %) was stirred for 24 hours at 25° C and worked up as for Example 3.

The desired product was isolated as a bottom oil in yield of 97% and purity of 96%.

EXAMPLE 5

Example 4 was repeated using the same reactants in the same quantities, except that only 0.15g (1 mole %) of tetrabutylammonium bromide was used. Essentially quantitative yield of the desired product was obtained after 5 hours at 70° C.

EXAMPLE 6

Example 4 was repeated using the same reactants in the same quantities except that 0.75g (5 mole %) of tetrabutylammonium bromide was used. Essentially quantitative yield of the desired product was obtained after 2 hours at 65° C.

EXAMPLE 7

A mixture of 2,2-dimethyl-3-(2',2'-dichlorovinyl)cyclopropane carboxylic acid (11.55g, 0.055M), water (50 mls), potassium carbonate, (3.7g, 0.0275M), 3-phenoxybenzyl bromide (13.15g, 0.05M), toluene (50 mls), and tetrabutylammonium bromide (0.75g, 5 mole %), was stirred at 65° C and yielded close to quantitative yield of the desired product after about 48 hours reaction time.

EXAMPLE 8

A mixture of 2,2-dimethyl-3-(2',2'-dichlorovinyl)cyclopropane carboxylic acid (311g, 1.49M), water (700 mls), potassium carbonate (104g, 0.75M), alpha-cyano-3-phenoxybenzyl bromide (395g, 1.37M) toluene (700 mls) and tetrabutylammonium bromide (4.4g, 1 mole %) was stirred at 65° C for 10 hours. The product was worked-up as described in Example 3 to give alpha-cyano-3-phenoxybenzyl-2,2-dimethyl-3-(2',2'-dichlorovinyl)cyclopropane carboxylate (550g). Yield based on alpha-cyano-3-phenoxybenzyl bromide was 96.5%.

EXAMPLE 9

A mixture of 2,2,3,3-tetramethylcyclopropane carboxylic acid (4.7kg,33M), water (12 liters), potassium carbonate (2.28kg, 16.5M), alpha-cyano-3-phenoxybenzyl bromide (8.64kg, 30M), toluene (15 liters) and tetrabutylammonium bromide (96g, 1 mole %) was stirred at 60° C for 5 hours.

A working-up procedure similar to that employed in Example 1 gave alpha-cyano-3-phenoxybenzyl-2,2,3,3-tetramethylcyclopropane carboxylate (9.280g, purity × 97%).

Yield based on starting benzyl bromide was 85.7%.

EXAMPLE 10

Example 2 was repeated using alpha-cyano-3-phenoxybenzyl chloride and 1 mole % tetrabutylammonium bromide as catalyst. A similar yield of the desired product was obtained after stirring the mixture at 90° C for 6 hours.

EXAMPLE 11

Example 6 was repeated using the same reactants in the same quantities except that 0.65g (5 mole %) of 1,4,7,10,13,16-hexaoxacyclooctadecane was used as catalyst. The mixture was stirred at 65° C for 20 hours and then worked-up as previously to give the desired product in 98.2% yield.

EXAMPLE 12

Example 6 was repeated except that no catalyst was added. After 120 hours at 65° C approximately 40% of the bromide had been converted to the desired product.

EXAMPLE 13

A mixture of cis-2,2-dimethyl-3-(2',2'-dibromovinyl)cyclopropane carboxylic acid (2.2g, 0.0074M), water (5 mls), potassium carbonate (0.5g, 0.0037M), alpha-cyano-3-phenoxybenzyl bromide (1.94g, 0.00674M), methylene chloride (35 mls), and tetrabutylammonium bromide (0.1g, 4.6 mole %) was stirred at 40° C for 10 hours. The product was worked-up as described in Example 3 to give cis-alpha-cyano-3-phenoxybenzyl-2,2-dimethyl-3-(2',2'-dibromovinyl)cyclopropane carboxylate (3.4g, 0.00673M). Yield based on alpha-cyano-3-phenoxybenzyl bromide was 99.9%.

EXAMPLE 14

Example 13 was repeated using trans-2,2-dimethyl-3-(2',2'-dibromovinyl) cyclopropanecarboxylic acid under the same reaction conditions and with the same quantities. Yield of the trans-ester based on alpha-cyano-3-phenoxybenzyl bromide was 100%.

EXAMPLE 15

Example 13 was repeated using (—) cis-2,2-dimethyl-3-(2',2'-dibromovinyl)cyclopropane carboxylic acid under the same reaction conditions and the same quantities. Yield based on alpha-cyano-3-phenoxybenzyl bromide was 100%; $[\alpha]_D = -11.1°$.

EXAMPLE 16

A mixture of (—) 2-(4-chlorophenyl)-3-methylbutyric acid (46.75g, 0.22M), potassium carbonate (15.2g, 0.11M), water (100ml), alpha-cyano-3-phenoxybenzyl bromide (57.6g, 0.2M), methylene chloride (150 ml) and tetrabutylammonium bromide (1.3g, 2 mole %) was stirred and refluxed for 24 hours. The desired product was isolated as a bottom oil (82.4g). Yield = 99.4%, purity = 97%; $[\alpha]_D = +7.3°$.

I claim:

1. A process for the preparation of a phenoxybenzyl ester of the formula

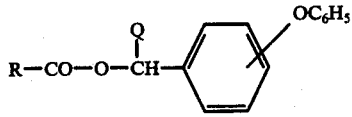

wherein Q is a hydrogen atom or a cyano group and R is a. a cyclopropyl group of the formula

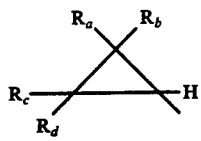

in which $R_a$ and $R_b$ each is an alkyl group containing from 1 to 6 carbon atoms, or a halogen atom of atomic number from 9 to 35, inclusive, or $R_a$ is a hydrogen atom and $R_b$ is an alkenyl group containing from 2 to 6 carbon atoms optionally substituted by from 1 to b 3 chlorine or bromine atoms, $R_c R_d$ each is an alkyl group containing from 1 to 6 carbon atoms, or $R_c$ is hydrogen and $R_d$ is $R_b$, or $R_a$ and $R_b$ together or $R_c$ and $R_d$ together is an alkylene group containing from 2 to 6 carbon atoms; or b. a benzyl group of the formula

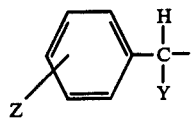

in which Z is a halogen atom of atomic number 9 to 35, inclusive, or an alkoxy group containing from 1 to 4 carbon atoms and Y is an alkyl group containing from 1 to 6 carbon atoms, which process comprises neutralizing an acid of the formula R-COOH in which R is defined above with a water-soluble base, and then contacting the resulting product with a solution in a water-immiscible organic solvent of a benzyl halide of the formula

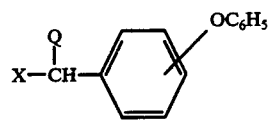

in which X is a halogen atom; and Q is defined above in the presence of a macrocyclic polyether phase-transfer catalyst.

2. A process according to claim 1 wherein X represents a chlorine or bromine atom.

3. A process according to claim 1 wherein the water-soluble base is an inorganic base.

4. A process according to claim 1 wherein the water-immiscible solvent is an organic liquid in which the benzyl halide is at least moderately soluble.

5. A process according to claim 1 wherein the phenoxybenzyl ester is an alpha-cyano-3-phenoxybenzyl ester of tetramethylcyclopropane carboxylic acid, dimethyl-dichlorovinyl-cyclopropane carboxylic acid, dimethyl-dibromovinyl-cyclopropane carboxylic acid, or 2-(4-chlorophenyl)-3-methylbutyric acid.

* * * * *